US011903830B2

(12) United States Patent
Carpentier (10) Patent No.: US 11,903,830 B2
(45) Date of Patent: Feb. 20, 2024

(54) PHYSIOLOGICALLY HARMONIZED REPAIR OF TRICUSPID VALVE

(71) Applicant: Edwards Lifesciences Corporation, Irvine, CA (US)

(72) Inventor: Alain F. Carpentier, Paris (FR)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 183 days.

(21) Appl. No.: 17/459,211

(22) Filed: Aug. 27, 2021

(65) Prior Publication Data

US 2021/0401577 A1    Dec. 30, 2021

Related U.S. Application Data

(60) Continuation of application No. 15/941,499, filed on Mar. 30, 2018, now abandoned, which is a division of
(Continued)

(51) Int. Cl.
*A61F 2/24*    (2006.01)

(52) U.S. Cl.
CPC .......... *A61F 2/2448* (2013.01); *A61F 2/2442* (2013.01); *A61F 2/2445* (2013.01); *A61F 2250/0018* (2013.01); *A61F 2250/0019* (2013.01)

(58) Field of Classification Search
CPC .................................................. A61F 2/2448
See application file for complete search history.

(56) References Cited

U.S. PATENT DOCUMENTS 3,656,185 A    4/1972 Carpentier
4,164,046 A    8/1979 Cooley
(Continued)

FOREIGN PATENT DOCUMENTS

EP    0338994 A1    10/1989
EP    0595791 A2    5/1994
(Continued)

OTHER PUBLICATIONS

Alonso-Lei, M.D., et al. Adjustable Annuloplasty for Tricuspid Insufficiency, The Annals of Thoracic Surgery, vol. 46, No. 3, pp. 368-369, Sep. 1988.
(Continued)

*Primary Examiner* — Jacqueline Woznicki
(74) *Attorney, Agent, or Firm* — Guy Cumberbatch (57) ABSTRACT

A prosthetic tricuspid remodeling annuloplasty ring having two free ends that are upturned in the inflow direction to help avoid unnecessary leaflet abrasion. The free ends are desirably separated across a gap that is large enough to reduce the risk of passing sutures through the conductive system of the heart, yet not too large that support of the septal leaflet of the tricuspid annulus is degraded. The tricuspid ring may have four sequential segments looking from the inflow side and extending in a clockwise direction from a free end located adjacent the antero septal commissure after implant. The ring may define an inflow bulge in the first segment and/or an inflow bulge in the fourth segment that help the ring conform to the natural bulges created by the adjacent aorta, thereby reducing stress and the potential for ring dehiscence. Desirably, the ring has variable flexibility, either gradual and/or between or within different segments, so as to adapt or harmonize its 3-dimensional shape to each individual patient.

20 Claims, 5 Drawing Sheets

Related U.S. Application Data application No. 13/600,040, filed on Aug. 30, 2012, now Pat. No. 9,937,041, which is a continuation of application No. 12/120,184, filed on May 13, 2008, now abandoned.

(56) References Cited

U.S. PATENT DOCUMENTS

| | | |
|---|---|---|
| 4,217,665 A | 8/1980 | Bex et al. |
| 4,489,446 A | 12/1984 | Reed |
| 4,602,911 A | 7/1986 | Ahmadi et al. |
| 4,917,698 A | 4/1990 | Carpentier et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,776,189 A | 7/1998 | Khalid |
| 5,824,066 A | 10/1998 | Gross |
| 5,824,069 A | 10/1998 | Lemole |
| 5,888,240 A | 3/1999 | Carpentier et al. |
| 5,972,030 A | 10/1999 | Garrison et al. |
| 6,001,127 A | 12/1999 | Schoon et al. |
| 6,019,739 A | 2/2000 | Rhee et al. |
| 6,024,918 A | 2/2000 | Hendriks et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,749,630 B2 | 6/2004 | McCarthy et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,294,148 B2 | 11/2007 | McCarthy |
| 7,329,280 B2 | 2/2008 | Bolling et al. |
| 7,367,991 B2 | 5/2008 | McCarthy et al. |
| 8,460,173 B2 | 6/2013 | Schweich, Jr. et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0083742 A1 | 5/2003 | Spence et al. |
| 2003/0093148 A1 | 5/2003 | Bolling et al. |
| 2003/0208264 A1 | 11/2003 | McCarthy et al. |
| 2004/0006384 A1 | 1/2004 | McCarthy |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1* | 6/2006 | McCarthy .............. A61F 2/2445 623/2.36 |
| 2006/0206203 A1 | 9/2006 | Yang et al. |
| 2008/0086203 A1 | 4/2008 | Roberts |
| 2008/0275551 A1 | 11/2008 | Alfieri |
| 2009/0036979 A1 | 2/2009 | Redmond et al. |
| 2009/0287303 A1 | 11/2009 | Carpentier |

FOREIGN PATENT DOCUMENTS

| | | |
|---|---|---|
| EP | 0860151 A1 | 8/1998 |
| EP | 1034753 A1 | 9/2000 |
| FR | 2708458 A1 | 5/1955 |
| WO | 9503757 | 2/1995 |
| WO | 0119292 A1 | 3/2001 |
| WO | 0126586 A1 | 4/2001 |
| WO | 0147438 A1 | 7/2001 |
| WO | 0187191 A1 | 11/2001 |
| WO | 0203892 A1 | 1/2002 |
| WO | 03020178 A1 | 3/2003 |
| WO | 03041617 A1 | 5/2003 |
| WO | 2004004607 A1 | 1/2004 |
| WO | 2005034813 A2 | 4/2005 |
| WO | 2005110290 A1 | 11/2005 |
| WO | 2005112830 A1 | 12/2005 |
| WO | 2007050506 A1 | 5/2007 |

OTHER PUBLICATIONS

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Carpentier-Edwards Classic Annuloplasty Ring With Duraflo Treatment Models 4425 and 4525 for Mitral and Tricuspid Valvuloplsty, Baxter Healthcare corporation, 1998.

Carpentier-Edwards Pyshio Annuloplasty Ring, Edwards Lifesciences Corporation, 2003.

(56) References Cited

OTHER PUBLICATIONS

Cochran, et al., Effect of Papillary Muscle Position on Mitral Valve Function: Relationship to Homografts, The Society of Thoracic Surgeons, pp. 5155-5161, 1998.

Cosgrove, Delos M, III, et al., Initial Experience with the Cosgrove-Edwards Annuloplasty System, The Annals of Thoracic Surgery, 1995; 60:499-504.

Cosgrove-Edwards Annuloplasty System (MED0004512), 2 pages, 2000.

D. de Caleya, et al., Fracture of Carpentier's Ring in a Patient with Tricuspid Annuloplasty, Thorac. Cardiovasc. Surgeon 31 (1983) p. 175-176.

D.C. Miller, IMR Redux—To Repair or Replace?, Journal of Thoracic & Cardiovascular Surgery, pp. 1 8,2001.

Edwards Lifesciences MC3Tricuspid Annuloplasty System brochure. Copyright 2006.

Galinanes, Manuel, et al., Fracture of the Carpentier-Edwards Ring in Tricuspid Position: A Report of Three Cases, Ann Thorac Surg 1986; 42:74-76.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH study Shows Mitral Valve Prolapse Not a Stroke Risk Factor, Massachusetts General Hospital, pp. 1-3, Jun. 1999.

Salgo, et al., Effect of Annular Shape on Leaflet curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical—Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000 .

Techniques for 3D Quantitative Echocardiography, University of Washington Cardiovascular Research & Training Center Cardiac Imaging Research Lab, pp. 1-5, Oct. 2003.

* cited by examiner

PHYSIOLOGICALLY HARMONIZED REPAIR OF TRICUSPID VALVE

CROSS REFERENCE TO RELATED APPLICATIONS

This application is a continuation of U.S. patent application Ser. No. 15/941,499, filed Mar. 30, 2018, which is a divisional of U.S. patent application Ser. No. 13/600,040, filed Aug. 30, 2012, now U.S. Pat. No. 9,937,041, which is a continuation of U.S. patent application Ser. No. 12/120,184, filed May 13, 2008, the entire disclosures all of which are incorporated by reference for all purposes.

FIELD OF THE INVENTION

The present invention relates generally to medical devices and particularly to a tricuspid annuloplasty ring.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique that has been shown to be effective in treating incompetence is annuloplasty, in which the deformed valve annulus is reshaped by attaching a prosthetic annuloplasty repair segment or ring to the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate of a metal such as rods or bands of stainless steel or titanium, or a flexible material such as silicone rubber or Dacron cordage, covered with a biocompatible fabric or cloth to allow the ring to be sutured to the fibrous annulus tissue. Annuloplasty rings may be stiff or flexible, split or continuous, and may have a variety of shapes, including circular, D-shaped, C-shaped, or kidney-shaped. Examples are seen in U.S. Pat. Nos. 5,041,130, 5,104,407, 5,201,880, 5,258,021, 5,607,471 and, 6,187,040 B1. Most annuloplasty rings are formed in a plane, with some D-shaped mitral rings being bowed along their straight side to conform to the shape of the annulus at that location. Whether totally flexible, rigid, or semi-rigid, annuloplasty rings have been associated with a 10% to 15% ring dehiscence incidence at 10 years, thus requiring a reoperation. The present invention is intended to reduce this complication.

Figure 1:
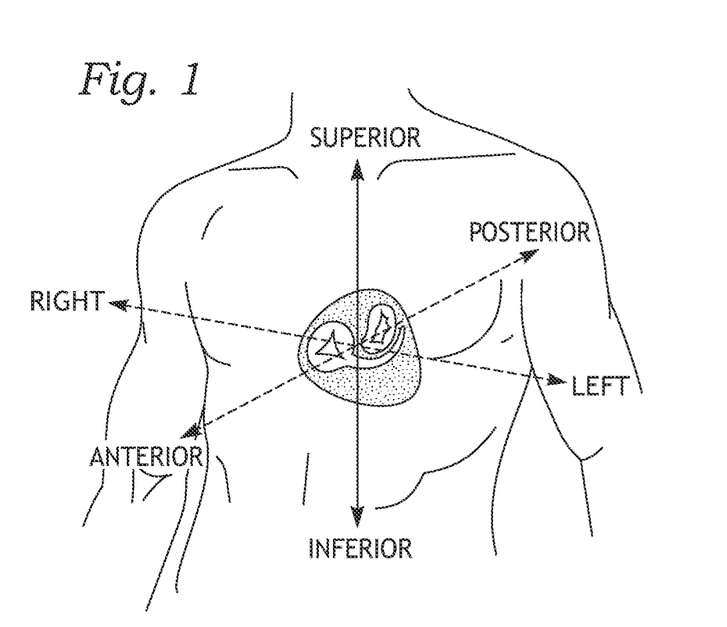
FIG. 1 is a schematic representation of the AV junctions within the heart and the body in the left anterior oblique projection.

For the purposes of anatomic orientation, please refer to FIG. 1, which is a schematic representation of the AV junctions within the heart and the body in the left anterior oblique projection. The body is viewed in the upright position and has 3 orthogonal axes: superior-inferior, posterior-anterior, and right-left. Traditional nomenclature for the AV junctions derives from a surgically distorted view, placing the valvular rings in a single horizontal plane with antero-posterior and right-left lateral coordinates. The descriptive terms used, however, are anatomically inaccurate. An accurate account of the coordinates of the valvular orifices is provided by the simple expedient of relating appropriately the view obtained in left anterior oblique projection to the supero-inferior and antero-posterior coordinates of the body.

Figure 2:
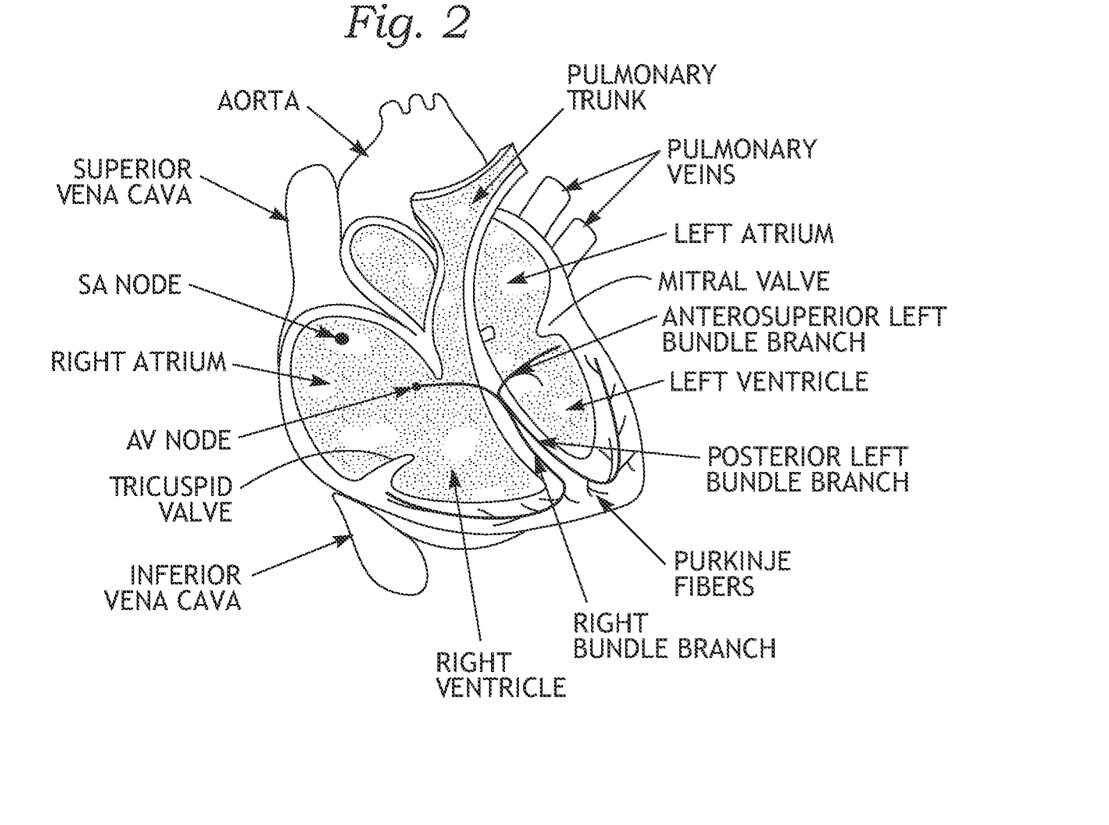
FIG. 2 is a cutaway view of the heart from the front, or anterior, perspective.

FIG. 2 is a cutaway view of the heart from the front, or anterior, perspective, with most of the primary structures marked. As is well known, the pathway of blood in the heart is from the right atrium to the right ventricle through the tricuspid valve, to and from the lungs, and from the left atrium to the left ventricle through the mitral valve. The present application has particular relevance to the repair of the tricuspid valve, which regulates blood flow between the right atrium and right ventricle, although certain aspects may apply to repair of other of the heart valves. The tricuspid and mitral valves together define the atrioventricular (AV) junctions.

As seen in FIG. 2, four structures embedded in the wall of the heart conduct impulses through the cardiac muscle to cause first the atria then the ventricles to contract. These structures are the sinoatrial node (SA node), the atrioventricular node (AV node), the bundle of His, and the Purkinje fibers. On the rear wall of the right atrium is a barely visible knot of tissue known as the sinoatrial, or SA node. This tiny area is the control of the heart's pacemaker mechanism. Impulse conduction normally starts in the SA node. It generates a brief electrical impulse of low intensity approximately 72 times every minute in a resting adult. From this point the impulse spreads out over the sheets of tissue that make up the two atria, exciting the muscle fibers as it does so. This causes contraction of the two atria and thereby thrusts the blood into the empty ventricles. The impulse quickly reaches another small specialized knot of tissue known as the atrioventricular, or AV node, located between the atria and the ventricles. This node delays the impulse for about 0.07 seconds, which is exactly enough time to allow the atria to complete their contractions. When the impulses reach the AV node, they are relayed by way of the several bundles of His and Purkinje fibers to the ventricles, causing them to contract. As those of skill in the art are aware, the integrity and proper functioning of the conductive system of the heart is critical for good health.

Figure 3:
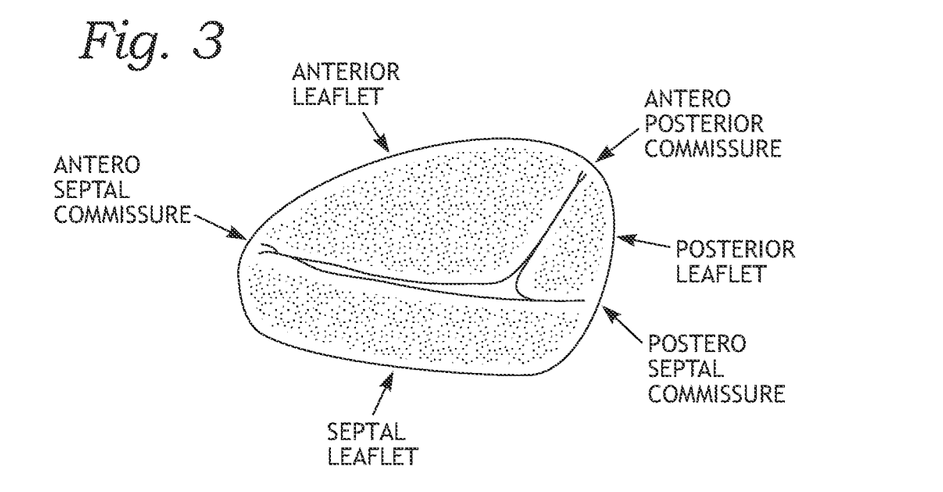
FIG. 3 is a schematic plan view of the tricuspid annulus with typical orientation directions noted as seen from the inflow side.

FIG. 3 is a schematic view of the tricuspid valve orifice seen from its inflow side (from the right atrium), with the peripheral landmarks labeled as: antero septal commissure, anterior leaflet, posterior commissure, antero posterior leaflet, postero septal commissure, and septal leaflet. Contrary to traditional orientation nomenclature, the tricuspid valve is nearly vertical, as reflected by these sector markings. From the same viewpoint, the tricuspid valve 20 is shown surgically exposed in FIG. 4 with an annulus 22 and three leaflets 24a, 24b, 24c extending inward into the flow orifice. Chordae tendineae 26 connect the leaflets to papillary muscles located in the RV to control the movement of the leaflets.

Figure 4:
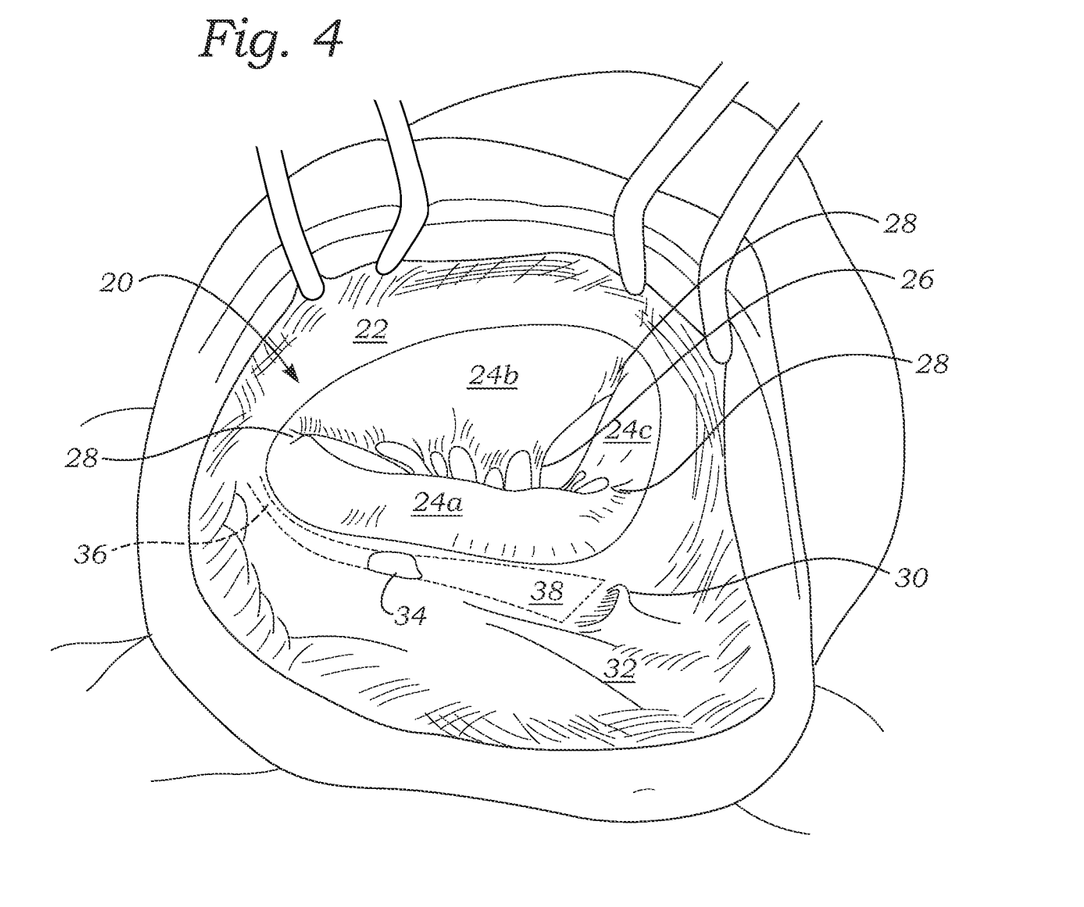
FIG. 4 is a plan view of the native tricuspid valve and surrounding anatomy from the inflow side.

The tricuspid annulus 22 is an ovoid-shaped fibrous ring at the base of the valve that is less prominent than the mitral annulus, but larger in circumference.

Reflecting their true anatomic location, the three leaflets in FIG. 4 are identified as septal 24a, anterior 24b, and posterior (or "mural") 24c. The leaflets join together over three prominent zones of apposition, and the peripheral intersections of these zones are usually described as commissures 28. The leaflets 24 are tethered at the commissures 28 by the fan-shaped chordae tendineae 26 arising from prominent papillary muscles originating in the right ventricle. The septal leaflet 24a is the site of attachment to the fibrous trigone, the fibrous "skeletal" structure within the heart. The anterior leaflet 24b, largest of the 3 leaflets, often has notches. The posterior leaflet 24c, smallest of the 3 leaflets, usually is scalloped.

The ostium 30 of the right coronary sinus opens into the right atrium, and the tendon of Todaro 32 extends adjacent thereto. The AV node 34 and the beginning of the bundle of His 36 are located in the supero-septal region of the tricuspid valve circumference. The AV node 34 is situated directly on the right atrial side of the central fibrous body in the muscular portion of the AV septum, just superior and anterior to the ostium 30 of the coronary sinus 30. Measuring approximately 1.0 mm×3.0 mm×6.0 mm, the node is flat and oval. The AV node 34 is located at the apex of the triangle of Koch 38, which is formed by the tricuspid annulus 22, the ostium 30 of the coronary sinus, and the tendon of Todaro 32. The AV node 34 continues on to the bundle of His 36, typically via a course inferior to the commissure 28 between the septal 24a and anterior 24b leaflets of the tricuspid valve; however, the precise course of the bundle of His 36 in the vicinity of the tricus valve may vary. Moreover, the location of the bundle of His 36 may not be readily apparent from a resected view of the right atrium because it lies beneath the annulus tissue.

The triangle of Koch 38 and tendon of Todaro 32 provide anatomic landmarks during tricuspid valve repair procedures. A major factor to consider during surgery is the proximity of the conduction system (AV node 34 and bundle of His 36) to the septal leaflet 24a. Of course, surgeons must avoid placing sutures too close to or within the AV node 34. C-shaped rings are good choices for tricuspid valve repairs because they allow surgeons to position the break in the ring adjacent the AV node 34, thus avoiding the need for suturing at that location.

Figures 5A, 5B:
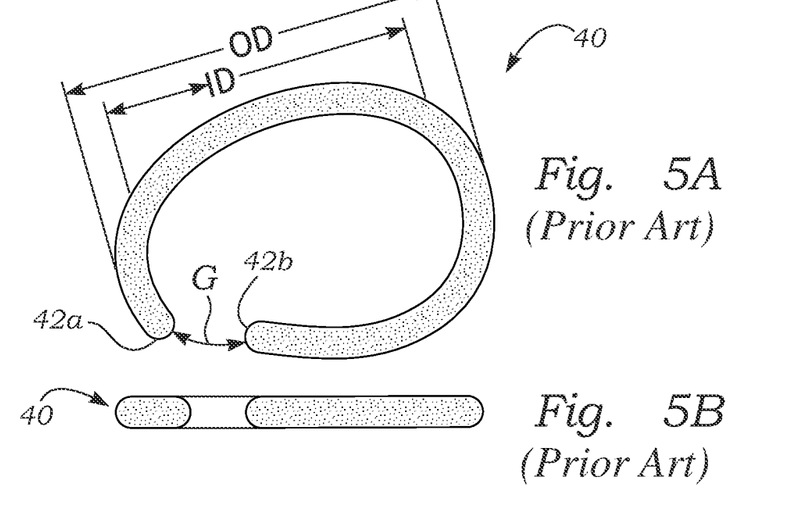
FIGS. 5A and 5B are plan and septal elevational views, respectively, of a planar tricuspid annuloplasty ring of the prior art.
Figure 6:
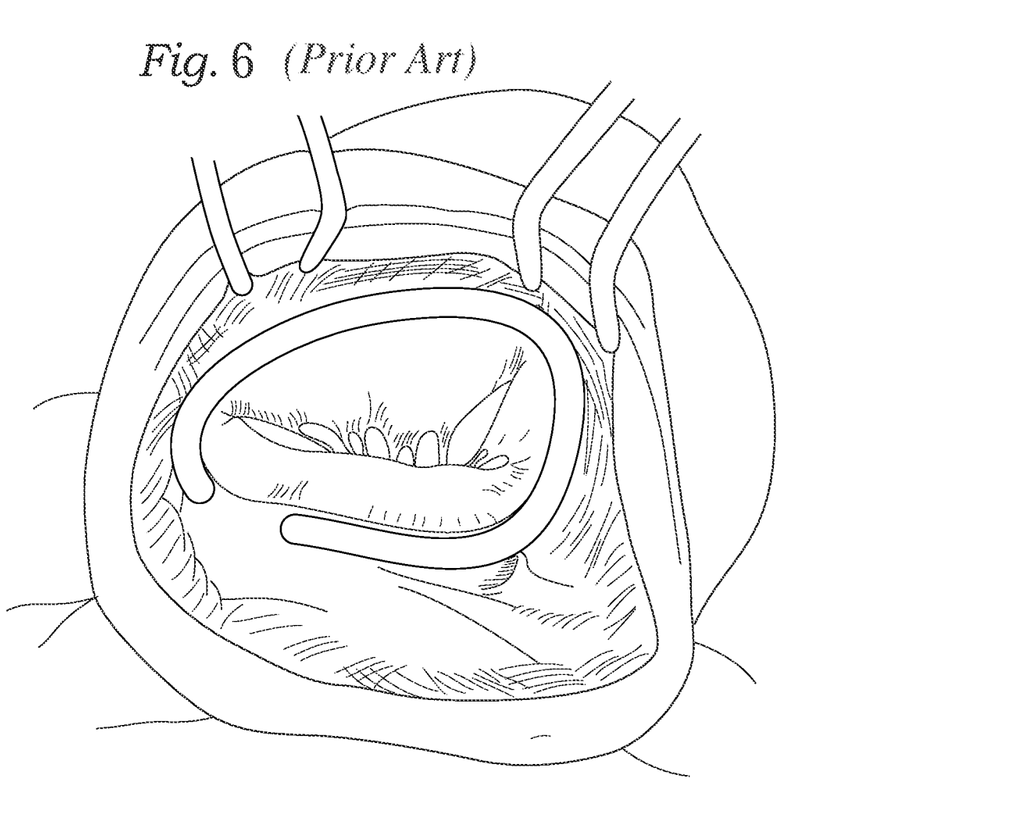
FIG. 6 is a plan view of the native tricuspid valve and surrounding anatomy from the inflow side with the annuloplasty ring of FIGS. 5A-5B implanted.

A rigid C-shaped ring of the prior art is the Carpentier-Edwards Classic® Tricuspid Annuloplasty Ring sold by Edwards Lifesciences Corporation of Irvine, CA, which is seen in FIGS. 5A and 5B. Although not shown, the planar ring 40 has an inner titanium core (not shown) covered by a layer of silicone and fabric. Rings for sizes 26 mm through 36 mm in 2 mm increments have outside diameters (OD) between 31.2-41.2 mm, and inside diameters (ID) between 24.3-34.3 mm. These diameters are taken along the "diametric" line spanning the greatest length across the ring because that is the conventional sizing parameter. A gap G between free ends 42a, 42b in each provides the discontinuity to avoid attachment over the AV node 34. The gap G for the various sizes ranges between about 5-8 mm, or between about 19%-22% of the labeled size. As seen in the implanted view of FIG. 6, the gap G is sized just larger than the AV node 34. Despite this clearance, some surgeons are uncomfortable passing sutures so close to the conductive AV node 34, particularly considering the additional concern of the bundle of His 36.

A flexible C-shaped tricuspid band is sold under the name Sovering™ by Sorin Biomedica Cardio S.p.A. of Via Crescentino, Italy. The Sovering™ band is made with a radiopaque silicone core covered with a knitted polyester (PET) fabric so as to be totally flexible. Bands for sizes 28 mm through 36 mm in 2 mm increments have outside diameters (OD) between 33.8-41.8 mm, and inside diameters (ID) between 27.8-35.8 mm. As with other tricuspid rings, a gap between the free ends provides a discontinuity to avoid attachment over the AV node. The nominal gap for the various sizes ranges of the Sovering™ band ranges between about 18-24 mm, or between about 60%-70% of the labeled size. Although this nominal gap helps avoid passing sutures close to the conductive AV node 34 and bundle of His 36, the band is designed to be attached at the commissures on either side of the septal leaflet and thus no support is provided on the septal side.

Despite numerous designs presently available or proposed in the past, there is a need for a prosthetic tricuspid ring that better harmonizes with the physiologic features of the tricuspid annulus, and in particular for a prosthetic tricuspid ring that better fits the contours of the tricuspid annulus and presents selective flexibility to reduce the stress in the attachment sutures, while at the same time reduces the risk of inadvertently passing a suture through the critical physiologic structures within the heart that conduct impulses.

SUMMARY OF THE INVENTION

The present invention provides a tricuspid annuloplasty ring including a ring body generally arranged in a plane and about an axis along an inflow-outflow direction, the ring body being discontinuous so as to define a first free end and a second free end separated across a gap, the two free ends being bent out of the plane in an inflow direction. Preferably, the two free ends are bent to have an axial height of between about 1-4 mm out of the plane.

Preferably, the ring body defines a generally asymmetric ovoid shape and extends in a clockwise direction from a first free end located adjacent the antero-septal commissure when implanted, as seen looking at the inflow side thereof, around a first segment, a second segment, a third segment, and a fourth segment that terminates in the second free end at a septal point. In one embodiment the ring body has an arcuate bulge out of the plane toward the inflow side at the first segment to accommodate an anatomical bulge of the aorta into the tricuspid annulus. In a further embodiment, the ring body has an arcuate bulge out of the plane toward the inflow side at the fourth segment. Still further, the ring body desirably has a varying flexibility and is stiffer adjacent the first free end than adjacent the second free end, or comprises at least one hinge point that is locally more flexible than adjacent segments. In one preferred construction, the ring body comprises a plurality of concentric peripheral bands having an axial dimension which is larger adjacent the first free end than adjacent the second free end. In a preferred embodiment, the ring has a long dimension in millimeters, and the free ends are separated by a distance of between about 40%-50% of the long dimension.

In accordance with another aspect of the invention, a prosthetic tricuspid annuloplasty ring having a long dimension in millimeters, comprises an asymmetric generally ovoid ring body. The ring body is generally arranged in a plane and about an axis along an inflow-outflow direction and is discontinuous so as to define two free ends. The ring body has a length and shape such that if a first free end is implanted adjacent an antero septal commissure of the tricuspid annulus, the ring body conforms to the tricuspid annulus and a second end is located adjacent a septal leaflet thereof, and the free ends are separated across a gap having a dimension of between about 40%-50% of the long dimension.

In the ring having a gap of between 40%-50% of the long dimension, the ring body extends in a clockwise direction from the first free end, as seen looking at the inflow side thereof, around a first segment, a second segment, a third segment, and a fourth segment that terminates in the second free end at a septal point. In one embodiment the ring body has an arcuate bulge out of the plane toward the inflow side at the first segment to accommodate an anatomical bulge of the aorta into the tricuspid annulus. In a further embodiment, the ring body has an arcuate bulge out of the plane toward the inflow side at the fourth segment. Still further, the ring body desirably has a varying flexibility and is stiffer adjacent the first free end than adjacent the second free end, or comprises at least one hinge point that is locally more flexible than adjacent segments.

In accordance with a still further aspect of the invention, a prosthetic tricuspid annuloplasty ring comprises an asymmetric generally ovoid ring body generally arranged in a plane and about an axis along an inflow-outflow direction with a first free end located adjacent an antero-septal commissure when implanted and a second free end located at a septal point. The ring body extends in a clockwise direction as seen looking at an inflow side from the first free end around a first segment, a second segment, a third segment, and a fourth segment that terminates in the second free end. The ring body has an arcuate bulge out of the plane toward the inflow side at the first segment so as to accommodate an anatomical bulge of the aorta into the tricuspid annulus. The ring body may also have an arcuate bulge out of the plane toward the inflow side at the fourth segment. Desirably, the ring body has a varying flexibility and the fourth segment is relatively more flexible than the third segment. The first free end may also be stiffer than the second free end. Alternatively, the varying flexibility comprises at least one hinge point that is locally more flexible than adjacent segments.

In a further embodiment, and prosthetic tricuspid annuloplasty ring is provided that comprises an asymmetric generally ovoid ring body generally arranged in a plane and about an axis along an inflow-outflow direction with a first free end located adjacent an antero-septal commissure when implanted and a second free end located at a septal point. The ring body extends in a clockwise direction as seen looking at an inflow side from the first free end around a first segment, an second segment, a third segment, and a fourth segment that terminates in the second free end. The ring body has a variable flexibility comprising at least one hinge point that is locally more flexible than adjacent segments. Desirably, the hinge point is located at the approximate midpoint of the ring body. Alternatively, there are two hinge points located approximately diametrically opposite one another so that the ring flexes generally in a plane.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides an improved tricuspid annuloplasty ring that better conforms to the native annulus and is shaped to protect certain features of the surrounding anatomy. The ring of the present invention is designed to support a majority of the tricuspid annulus without risking injury to the leaflet tissue and heart's conductive system, such as the AV node 34 and bundle of His 36 (see FIG. 4). Additionally, the present ring is contoured to better approximate the three-dimensional shape of the tricuspid annulus; specifically, the ring is substantially planar but includes a bulge in the inflow direction at the location of the bulge created by the adjacent aorta. The bulge helps reduce stress between the ring and surrounding tissue, and thus the potential for tearing or ring dehiscence.

Another feature that matches the present tricuspid ring with the physiological features of the annulus is a variable flexibility from a relatively stiff first segment to a relatively flexible fourth segment. This varying flexibility permits the ring to adapt (harmonize) its motion and 3-dimensional shape to that of the annulus, rather than impose its own motion and 3-D geometry thereto which tends to increase the risk of ring dehiscence. In particular, the motion of the tricuspid annulus during systole-diastole is believed to exert some torsional forces on the implanted ring, and the variable flexibility accommodates such torques. Moreover, localized points of flexibility or "hinges" around the ring as described herein may best conform and harmonize the physical properties of the ring to the annulus motion, while at the same time providing the needed corrective support.

It should also be understood that certain features of the present tricuspid ring might also be applicable and beneficial to rings for other of the heart's annuluses. For instance, the present ring includes upturned or bent free ends that help reduce abrasion on the adjacent leaflets. The same structure might be used in a discontinuous ring for the mitral valve annulus.

The term "axis" in reference to the illustrated ring, and other non-circular or non-planar rings, refers to a line generally perpendicular to the ring that passes through the area centroid of the ring when viewed in plan view. "Axial" or the direction of the "axis" can also be viewed as being parallel to the direction of blood flow within the valve orifice and thus within the ring when implanted therein. Stated another way, the implanted tricuspid ring orients about a central flow axis aligned along an average direction of blood flow through the tricuspid annulus. Although the rings of the present invention are 3-dimensional, portions thereof are planar and lie perpendicular to the flow axis.

Figures 7A, 7B, 7C:
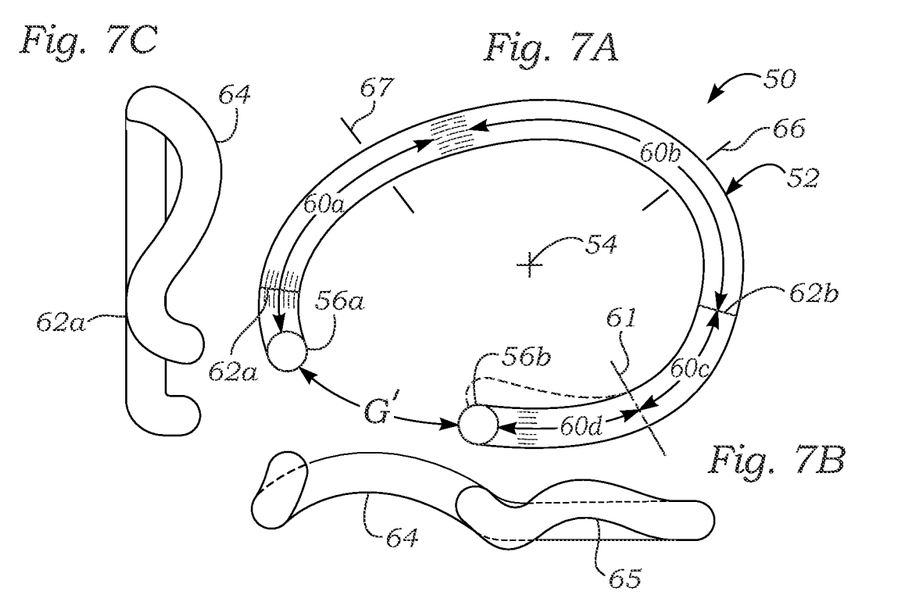
FIGS. 7A-7C are plan and septal and anterior elevational views, respectively, of an exemplary tricuspid annuloplasty ring of the present invention illustrating its free ends bent toward the inflow side and an aortic bulge and a septal bulge.

FIGS. 7A-7C illustrate, in plan and septal and anterior elevational views, a tricuspid ring 50 of the present invention having a ring body 52 generally arranged about an axis 54 and being discontinuous so as to define two free ends 56a, 56b. The axis 54 in FIG. 7A lies at the centroid of the ring or along of the axis of blood flow through the ring 50 when implanted, and it will be understood that the relative directions up and down are as viewed in FIG. 7B. Using this convention, the ring 50 is designed to be implanted in a tricuspid annulus such that blood will flow in the downward direction.

Figures 9A, 9B, 9C, 10A, 10B, 10C, 10D:
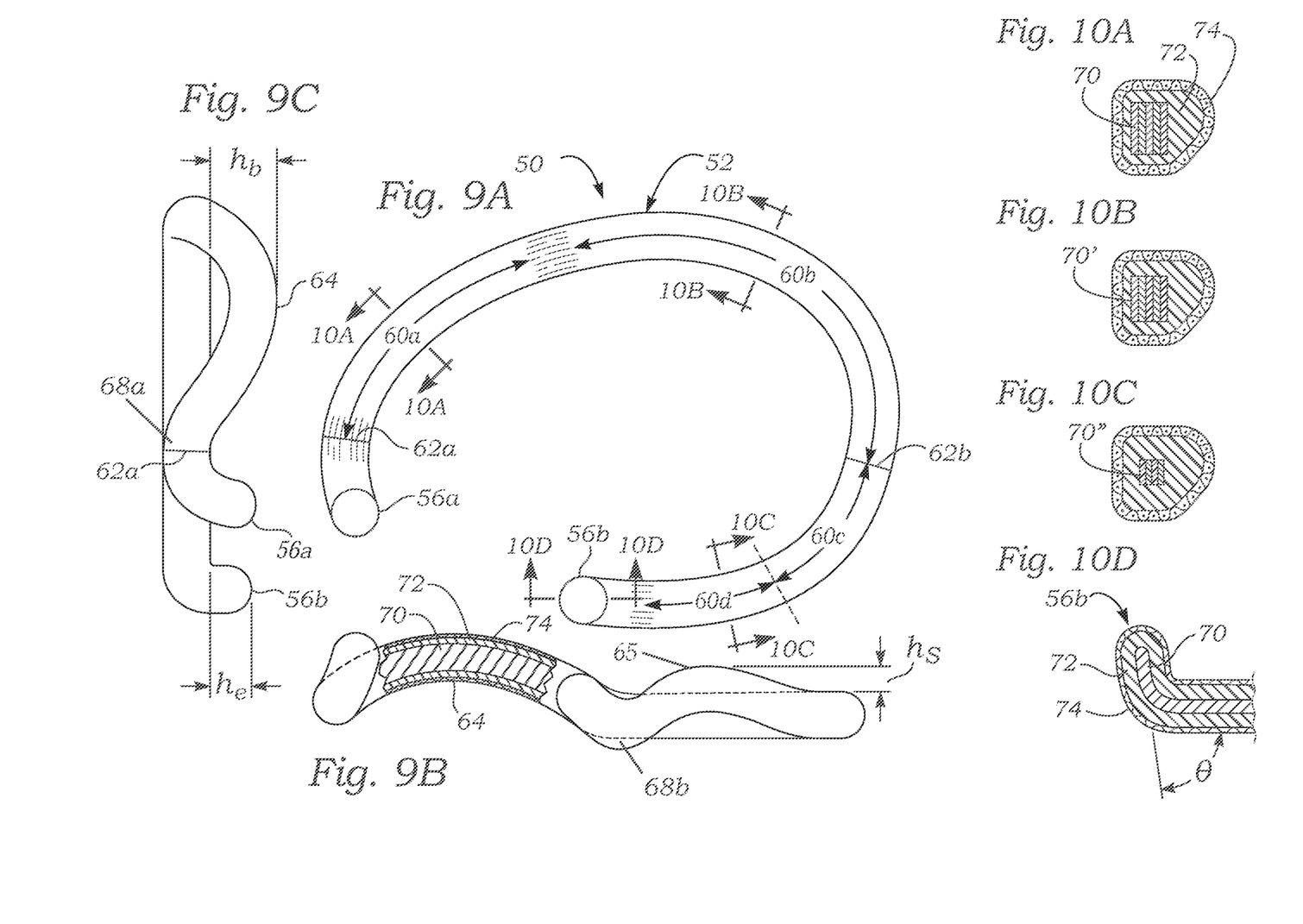
FIGS. 9A-9C are plan and septal and anterior elevational views, respectively, of the exemplary tricuspid annuloplasty ring of FIGS. 7A-7B with portions cutaway to show internal details.
FIGS. 10A-10D are sectional views taken along respective section lines in FIG. 9A.

As seen in FIGS. 7A-7C and also in FIGS. 9A-9C, the ring body 52 is substantially asymmetric and ovoid with the first free end 56a located adjacent the antero-septal commissure (see FIG. 3). The ring body 52 extends in a clockwise direction, as seen looking at the inflow side in FIG. 7A, around a first segment 60a corresponding to the aortic part of the anterior leaflet, a second segment 60b corresponding to the remaining part of the anterior leaflet and ending at the postero septal commissure, a third segment 60c from the postero septal commissure to a line 61 part way along the septal leaflet, and a fourth segment 60d that terminates in the second free end 56b at a septal point. The nomenclature for these segments is taken from the standard anatomical nomenclature around the tricuspid annulus as seen in FIG. 3.

The precise relative dimensions of the segments may vary, but they are generally as indicated in the view of FIG. 7A. That is, the second segment 60b is the largest, followed by the first segment 60a, and then the smaller third segment 60c and fourth segment 60d. It should be further noted that the term "asymmetric" means that there are no planes of symmetry through the ring body 52 looking from the inflow side, and "ovoid" means generally shaped like an egg with a long axis and a short axis, and one long end larger than the other.

Figure 8:
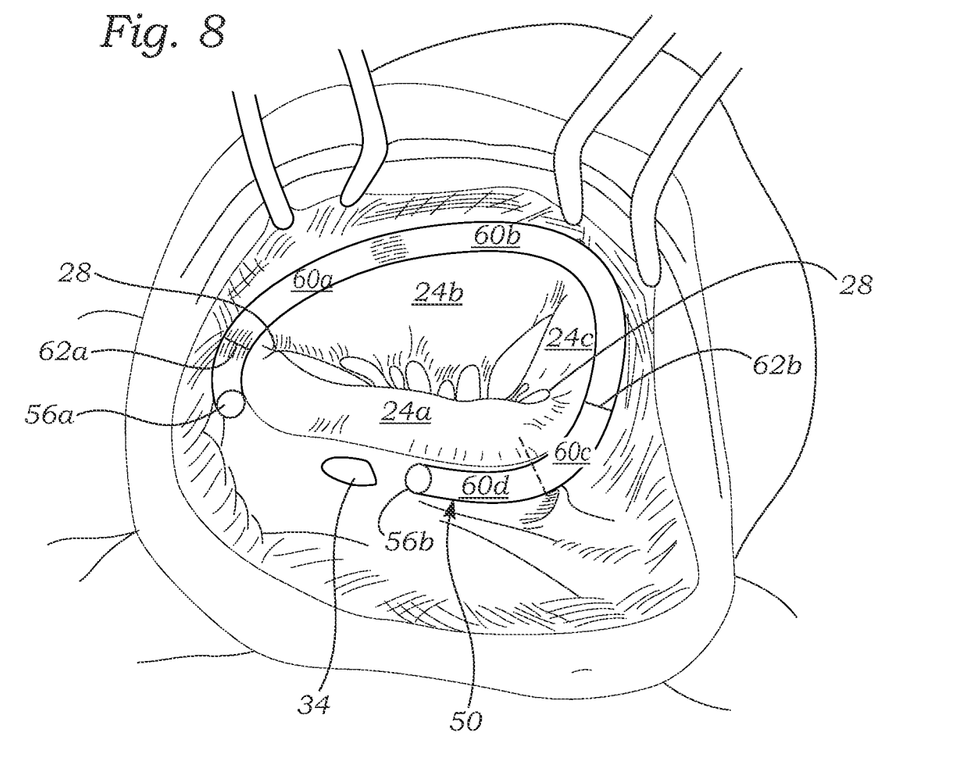
FIG. 8 is a plan view of the native tricuspid valve and surrounding anatomy from the inflow side with the annuloplasty ring of FIGS. 7A-7B implanted.

FIG. 8 shows the tricuspid ring 50 in plan view after having been implanted or otherwise affixed to a tricuspid valve. To quantify relative to the native anatomy, the combined first and second segments 60a and 60b extend approximately around the tricuspid annulus between the two commissures 28 that bookend the septal leaflet 24a. Accordingly, a pair of commissure markers 62a, 62b on the exterior of the ring body 52 facilitate implantation by registering the ring 50 with respect to the commissures 28. The markers 62a, 62b are typically radially-oriented colored thread fastened to a fabric covering on the ring.

A majority of the ring body 52 is planar except for the free ends 56a, 56b which are upturned and the first segment 60a and a part of fourth segment 60d that are bowed upward. (To repeat, the "up" direction is merely for purpose of clarity herein and is synonymous with the inflow direction). As with existing rings, sizes 26 mm through 36 mm in 2 mm increments are available having outside diameters (OD) between 31.2-41.2 mm, and inside diameters (ID) between 24.3-34.3 mm. Again, these diameters are taken along the "diametric" line spanning the greatest length across the ring, as seen in FIG. 5A. It should be mentioned that the present invention is not limited to the aforementioned range of sizes, and rings smaller than 26 mm or larger rings of 38 or 40 mm OD are also possible, for example.

A gap G' between the two free ends 56a, 56b is substantially larger than in certain rings of the prior art to reduce the risk of suturing into the AV node or bundle of His, and to accommodate variations in anatomy and location of the bundle of His. In particular, the gap G' is preferably between about 40%-50% of the labeled size, preferably between about 43-45%. In one configuration, the gap G' is about 40% of the size of the long axis of the ring, which is typically the labeled size in millimeters. In absolute terms, the gap G' is desirably between about 10-18 mm, depending on the labeled size. For instance, the gap G' is preferably about 13.6 mm for a size 34 ring (about 40% of the labeled size). On the other hand, the gap G' is not too large to reduce the effective support for the septal leaflet 24a. Preferably, the fourth segment 60d of the ring 50 of the present invention extends at least half of the way around the septal leaflet 24a.

In a preferred embodiment, the gap G' is larger than the gap G in the rigid C-shaped Carpentier-Edwards Classic® Tricuspid Annuloplasty Ring, seen in FIGS. 5A and 5B. The gap G for the various sizes of Classic® Rings ranges between about 5-8 mm, or between about 19%-22% of the labeled size. At the same time, the gap G' of the ring of the present invention is smaller than the gap in the flexible C-shaped Sovering™ tricuspid ring from Sorin Biomedica Cardio S.p.A. The gap for the various sizes of the Sovering™ ranges between about 18-24 mm, or between about 60%-70% of the labeled size. Therefore, the gap G' of the ring of the present invention is preferably greater than 8 mm and less than 18 mm, or is between about 23%-59% of the labeled size (typically equal to the dimension in millimeters of the long axis of the ring).

The free ends 56a, 56b of the exemplary ring 50 are upturned in the inflow direction so as to help reduce abrasion on the adjacent leaflets (septal, or both septal and antero-superior). Prior rings that are not completely flexible terminate in ends that are extensions of the ring periphery, that is, they do not deviate from the paths that the adjacent segments of the ring follow. As will be explained below, the present ring 50 desirably includes a core member that provides at least some rigidity and structural support for the annulus. The upturned ends 56a, 56b present curved surfaces that the constantly moving leaflets might repeatedly contact, as opposed to point surfaces so that forcible abrasion of the moving leaflets in contact with the ends of the ring is avoided.

As seen in FIGS. 7B and 7C, the exemplary ring 50 also includes an upward arcuate bow or bulge 64 in the first segment 60a, and another upward bulge 65 in the fourth segment 60d. The "aortic" bulge 64 accommodates a similar contour of the tricuspid annulus due to the external presence of the aorta and desirably extends from near the first free end 56a along first segment 60a to a location that corresponds to the end of the aortic part of the anterior leaflet. Prior tricuspid rings are substantially planar, and if at all rigid they necessarily deform the annulus to some extent at this location. The aortic bulge 64 helps reduce stress upon implant and concurrently reduces the chance of dehiscence, or the attaching sutures pulling out of the annulus. The axial height $h_b$ of the aortic bulge 64 above the nominal top surface of the ring body 52, as indicated in FIG. 9C, is between about 3-9 mm, preferably about 6 mm. The "septal" bulge 65 conforms to the slight bulging of the septal leaflet attachment in this area. The axial height $h_s$ of the septal bulge 65 above the nominal top surface of the ring body 52, as indicated in FIG. 9B, is between about 2 to 4 mm. These two bulges 64, 65 provide a "saddle shape" to the ring body 52. Since each bulge 64, 65 rises up and then down, and since each of the adjacent free ends 56a, 56b curves upward, transitional downward bends 68a, 68b are formed between each bulge and free end as shown.

Now with particular reference to FIGS. 9A-9C and 10A-10D, the tricuspid ring 50 of the present invention is seen partially cutaway and in sections to illustrate further exemplary features. As seen best in the cutaway portion of FIG. 9B, the ring body 52 preferably comprises an inner core 70 encompassed by an elastomeric interface 72 and an outer fabric covering 74.

The inner core 70 extends substantially around the entire periphery of the ring body 52 and is a relatively rigid material such as stainless steel, titanium, Elgiloy (an alloy primarily including Ni, Co, and Cr), Nitinol, and even certain polymers. The term "relatively rigid" refers to the ability of the core 70 to support the annulus without substantial deformation, and implies a minimum elastic strength that enables the ring to maintain its original shape after implant even though it may flex somewhat. Indeed, as will be apparent, the ring desirably possesses some flexibility around its periphery. To further elaborate, the core 70 would not be made of silicone, which easily deforms to the shape of the annulus and therefore will not necessarily maintain its original shape upon implant.

The elastomeric interface 72 may be silicone rubber molded around the core 70, or a similar expedient. The elastomeric interface 72 provides bulk to the ring for ease of handling and implant, and permits passage of sutures though not significantly adding to the anchoring function of the outer fabric covering 74. The fabric covering 74 may be any biocompatible material such as Dacron® (polyethylene terephthalate). As seen in FIGS. 10A-10C, the elastomeric interface 72 and fabric covering 74 project outwards along the outside of the ring 50 to provide a platform through which to pass sutures. An alternative interface is simply wrapped, bunched or rolled fabric, with no silicone.

As mentioned above, the ring 50 of the present invention may possess a varying flexibility around its periphery. In general, the ring 50 is desirably stiffer adjacent the first free end 56a than adjacent the second free end 56b, and preferably has a gradually changing degree of flexibility for at least a portion in between. For instance, the first segment 60a may be relatively stiff while the remainder of the ring body 52 gradually becomes more flexible through the second segment 60b, third segment 60c, and fourth segment 60d. In a preferred embodiment, the fourth segment 60d is more flexible than the third segment 60c.

With reference to FIG. 7A, the reader will appreciate that the flexibility of the fourth segment 60d accommodates the inward movement of the annulus in that sector from fluid dynamic closing forces on the valve, and therefore reduces the chance of dehiscence. More particularly, radial forces exerted on the ring in the vertical direction, or along the small axis, will act on the flexible fourth segment 60d and proportionately bend it inward, as indicated in phantom. This reduction in the antero-septal ring dimension, in turn, will reduce tension on the native valve leaflets that pull inward from valve closing forces. Tests have been conducted to determine the amount of force and movement associated with the septal aspect of the tricuspid annulus in both systole and diastole. Consequently, a preferred flexibility for the fourth segment 60d has been determined and quantified in terms of the amount of desirable deformation under a given load. In one embodiment, the flexibility of the fourth segment 60d is such that it deforms inward by about 10% of the antero-septal (small axis) ring dimension under maximum load, typically resulting from right ventricular pressures of up to 70 mm Hg. In contrast, left ventricular pressures of up to 120 mm Hg are handled by a more robust mitral annulus. The tricuspid annulus is more fragile and implanted annuloplasty rings are somewhat more prone to dehiscence.

Another potential configuration of variable flexibility consists of one or more points of localized flexibility, or "hinge points," that may supplement the aforementioned gradually changing stiffness or be incorporated into an otherwise constant stiffness ring. The locations of the contemplated hinges are best described with reference to FIGS. 7A and 7B.

A central hinge created by an area of the ring body 52 that is locally more flexible than adjacent sectors is desirably located mid-way along the second segment 60b, as indicated by a hinge line 66. This hinge is located approximately at the center of the length of the ring body 52, and permits the segments on either side to flex or twist with respect to one another. Alternatively or in addition, two generally diametrically-opposed hinge points indicated by hinge lines 61 and 67 may be provided. These hinges are located at the upward bulges 64, 65 in the ring body 52, and provide "saddle" flexibility so that the ring flexes generally in a plane intersecting the bulges. A ring according to the present invention may have one or more of these hinges. Also, as mentioned above, the discrete hinges or points of flexibility may be incorporated into rings having constant or variable flexibility, as described above. Finally, though 3-dimensional rings are shown, the several embodiments of flexibility described herein may also be provided in a flat, planar tricuspid ring, and with or without the increase gap between the free ends.

In one exemplary construction, the ring body 52 includes a core 70 made of a plurality of concentric peripheral bands having an axial dimension which is larger adjacent the first free end 56a than adjacent the second free end 56b. Sectional FIGS. 10A-10C illustrate this embodiment. The core 70 in the first segment 60a (and possibly in a portion of the second segment 60b) is as seen in FIG. 10A, with six (6) concentric bands of a material such as Elgiloy. In the section of FIG. 10B, which is taken through the second segment 60b, a section of the core 70' still comprises six concentric bands, but its axial height is reduced relative to the height of the core as seen in FIG. 10A. Finally, FIG. 10C shows a section through the third segment 60c wherein a further section of the core 70" is further reduced in height but also only comprises four (4) concentric bands, with two of the bands having terminated or tapered off somewhere between sections 10B and 10C. Of course, this construction is entirely exemplary and the core 70 could also be made of a single integral member that gradually tapers down in size, among other alternatives. Several other alternatives are disclosed in U.S. Pat. No. 5,104,407 to Lam, et al., the disclosure of which is expressly incorporated herein by reference.

FIG. 10D shows the internal structure of the ring body 52 at the second end 56b. The core 70 is shown bending upward into close proximity with the extreme tip of the free end 56b, though it is protected by the elastomeric interface 72 and the outer fabric covering 74. Desirably, the core 70 has its greatest flexibility at this location, which is mid-way around the septal leaflet side of the tricuspid annulus. The upward bend of the core 70 and ring body 52 desirably makes an angle θ of between 45°-90°, preferably greater than 60°. Furthermore, the axial height $h_e$, as indicated in FIG. 9C, of the free ends 56a, 56b above the nominal top surface of the ring body 52 is between about 1-4 mm, preferably about 2 mm, and preferably the two free ends project upward the same distance (although such a configuration is not an absolute requirement). Because of the flexibility of the ring body 52 at the second end 56b, there may be a reduction in the antero-septal dimension of the ring depending on the load applied by the annulus in the small axis (vertical) dimension. Moreover, the second end 56b of the ring body 52 flexes more easily up and down, or in the axial dimension, which is believed to be beneficial in reducing dehiscence.

Another possible construction of the ring body 52 is a solid titanium (or suitable alternative) core extending from the first free end 56a to the second free end 56b. The areas of increased flexibility or discrete hinge points can be formed by reducing the cross-sectional shape of the core at those locations. For example, to obtain greater up and down flexibility, the axial height of the core is reduced at a point or along a region. A particularly desirable result of any partially flexible core is ring flexibility "out of the plane" to allow the ring to accommodate different patient geometries, while maintaining ring stiffness in the "plane." In this sense, the "plane" is the nominal plane in which the majority of the annulus/ring resides. One of skill in the art will understand that any of the embodiments described herein, and combinations thereof, may be created by shaping a solid material core.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method of repairing a native tricuspid annulus of a heart with a physiologically harmonized tricuspid annuloplasty ring, the tricuspid annulus defining a periphery as seen looking at an inflow side that has an asymmetric ovoid shape including the following anatomical landmarks as seen in series in a clockwise direction: an antero-septal commissure, an anterior leaflet on an anterior side, an antero-posterior commissure, a posterior leaflet on a posterior side, a postero-septal commissure, and a septal leaflet on a septal side, the tricuspid annulus further having a long dimension extending approximately from the antero-septal commissure to the postero-septal commissure with the septal leaflet extending therebetween, and wherein the septal leaflet is located radially inward of electrical structure of the heart including an atrioventricular node (AV node) and a bundle of His extending clockwise from the AV node, the method comprising:

advancing a tricuspid annuloplasty ring to the tricuspid annulus, the tricuspid annuloplasty ring having an inner core made of a relatively rigid material surrounded by a suture-permeable outer cover that conforms to the inner core, the inner core defining a central open area and defining a peripheral plan view shape lying partially in a plane and having an inflow side and an outflow side, wherein the plan view shape as seen looking at the inflow side has an asymmetric entirely outwardly convex ovoid open ring shape from a first free end extending clockwise to a second free end, the free ends being separated by a gap, and the outer cover having thereon a pair of commissure markers, wherein the first and second free ends are each bent into bends in the inflow direction from the plane at an angle θ of between 45°-90°, and wherein the cross-section of the inner core at the first and second free ends is such that the inner core is stiffer adjacent the first free end than adjacent the second free end, and the inner core has a varying flexibility that gradually becomes more flexible in a direction extending from the first free end to the second free end;

registering the commissure markers with the antero-septal commissure and the postero-septal commissure, respectively, such that the first free end extends counter-clockwise from the antero-septal commissure and the second free end extends clockwise from the postero-septal commissure, the second free end avoiding extending as far as the AV node; and suturing the tricuspid annuloplasty ring to the tricuspid annulus.

2. The method of claim 1, wherein the annuloplasty ring has a labeled ring size in millimeters equal to the dimension in millimeters of a long axis of the ring and corresponding to the long dimension of the tricuspid annulus, and the gap is between 23%-59% of the labeled ring size;.

3. The method of claim 2, wherein the gap is between 40%-50% of the labeled ring size.

4. The method of claim 1, wherein the gap is between 10-18 mm.

5. The method of claim 2, wherein when implanted at the tricuspid annulus the plan view shape as seen looking at the inflow side includes the following elements connected in series in a clockwise direction: the first free end located counter-clockwise from the antero-septal commissure, a first segment which extends around part of the anterior leaflet, a second segment which is larger than the first segment corresponding to a remaining part of the anterior leaflet and ending at the postero-septal commissure, a third segment which extends from the postero-septal commissure to part way along the septal leaflet that is smaller than the first segment, and a fourth segment which is smaller than the first segment that terminates in the second free end at a septal point on the tricuspid annulus, the second and third segments extending around a large end of the ovoid shape.

6. The method of claim 5, wherein the inner core has a varying flexibility and the fourth segment is relatively more flexible than the third segment.

7. The method of claim 5, wherein the inner core has a varying flexibility and the first and second segments have different flexibilities with regard to up and down bending.

8. The method of claim 5, wherein:
the second segment lies in the plane while a majority of the other segments are out of the plane, and
the inner core has at least one arcuate bulge out of the plane toward the inflow side defining a path that rises up and down.

9. The method of claim 8, wherein the arcuate bulge is an aortic arcuate bulge located at the first segment to accommodate an anatomical bulge of an aorta into the tricuspid annulus.

10. The method of claim 9, further including a septal arcuate bulge located at the fourth segment.

11. The method of claim 2, wherein the first and second free ends are bent in an inflow direction from the plane at an angle θ of between 45°-90°, wherein portions of the inner core adjacent both free ends angle downward so that a downward bend is formed between the free ends and the adjacent portions, and the first and second free ends are each bent to have a height of between 1-4 mm from a respective adjacent downward bend.

12. The method of claim 1, wherein the tricuspid annuloplasty ring has a labeled ring size in millimeters equal to a dimension in millimeters of a long axis of the ring and corresponding to the long dimension of the tricuspid annulus, and the gap is between 40%-50% of the labeled ring size.

13. The method of claim 12, wherein the gap is between 10-18 mm.

14. The method of claim 1, wherein when implanted at the tricuspid annulus the plan view shape as seen looking at the inflow side includes the following elements connected in series in a clockwise direction: the first free end located counter-clockwise from the antero-septal commissure, a first segment which extends around part of the anterior leaflet, a second segment which is larger than the first segment corresponding to a remaining part of the anterior leaflet and ending at the postero-septal commissure, a third segment which extends from the postero-septal commissure to part way along the septal leaflet that is smaller than the first segment, and a fourth segment which is smaller than the first segment that terminates in the second free end at a septal point on the tricuspid annulus, the second and third segments extending around a large end of the ovoid shape.

15. The method of claim 14, wherein the inner core has a varying flexibility and the fourth segment is relatively more flexible than the third segment.

16. The method of claim 14, the first segment is relatively stiff while the remainder of the inner core gradually becomes more flexible through the second segment, third segment, and fourth segment.

17. The method of claim 14, wherein:
the second segment lies in the plane while a majority of the other segments are out of the plane, and
the inner core has at least one arcuate bulge out of the plane toward the inflow side defining a path that rises up and down.

18. The method of claim 17, wherein the arcuate bulge is an aortic arcuate bulge located at the first segment to accommodate an anatomical bulge of an aorta into the tricuspid annulus.

19. The method of claim 18, further including a septal arcuate bulge located at the fourth segment.

20. The method of claim 1, wherein the bends at the first and second free ends each commences in close proximity with an extreme tip of the respective first or second free end, and wherein adjacent portions of the inner core adjacent both free ends angle downward so that a downward bend is formed between the free ends and the adjacent portions, and the first and second free ends are each bent to have a height of between 1-4 mm from a respective adjacent downward bend.

* * * * *